United States Patent
Katou et al.

(10) Patent No.: US 7,722,815 B2
(45) Date of Patent: *May 25, 2010

(54) CHEMICAL ANALYSIS APPARATUS AND CHEMICAL ANALYSIS METHOD

(75) Inventors: Hajime Katou, Chiyoda (JP); Ryo Miyake, Tsukuba (JP); Hiroyasu Uchida, Hitachinaka (JP); Katsuhiro Kambara, Hitachinaka (JP); Takenori Okusa, Hitachinaka (JP); Shigenori Watari, Hitachinaka (JP); Yoichiro Suzuki, Hitachinaka (JP); Tomonori Mimura, Tomobe (JP); Miki Taki, Hitachinaka (JP); Akira Inagaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 883 days.

This patent is subject to a terminal disclaimer.

(21) Appl. No.: 10/347,384

(22) Filed: Jan. 21, 2003

(65) Prior Publication Data

US 2003/0166260 A1 Sep. 4, 2003

(30) Foreign Application Priority Data

Mar. 1, 2002 (JP) ............................. 2002-055178

(51) Int. Cl.
*G01N 21/00* (2006.01)

(52) U.S. Cl. .................... 422/82.05; 422/50; 73/861.25; 73/1.82

(58) Field of Classification Search ............. 422/64, 422/127, 82.05, 50, 224; 436/43; 331/40; 73/861.25, 861.26, 1.82, 587

See application file for complete search history.

(56) References Cited

U.S. PATENT DOCUMENTS

| 3,614,069 | A | | 10/1971 | Murry |
| 5,379,785 | A | * | 1/1995 | Ohmori et al. .............. 134/184 |
| 5,596,989 | A | | 1/1997 | Morita |
| 5,665,605 | A | | 9/1997 | Coakley et al. |
| 5,736,100 | A | | 4/1998 | Miyake et al. |
| 6,197,255 | B1 | * | 3/2001 | Miyake et al. ................ 422/64 |
| 6,737,021 | B2 | | 5/2004 | Watari et al. |
| 7,004,016 | B1 | | 2/2006 | Puskas |

FOREIGN PATENT DOCUMENTS

| EP | 1 128 185 A2 | | 8/2001 |
| JP | 61-035831 | | 2/1986 |
| JP | 03-055044 | | 3/1991 |
| JP | 07-184898 | | 7/1995 |
| JP | 08-146007 | | 6/1996 |
| JP | 2000-146986 | * | 5/2000 |
| JP | 2001-242177 | * | 9/2001 |

OTHER PUBLICATIONS

Halacinski B et al. "Ultrasonic mixer for paints and emulsions", Ultrasonics Symposium, 1994, Proceedings, 1994 IEEE pp. 521-523.

* cited by examiner

*Primary Examiner*—Jill Warden
*Assistant Examiner*—Natalia Levkovich
(74) *Attorney, Agent, or Firm*—Antonelli, Terry, Stout & Kraus, LLP.

(57) ABSTRACT

Provided is a chemical analysis apparatus comprising a mechanism which can efficiently agitate a substance to be agitated so that a sample and a reagent are agitated and mixed together in a shorter time with a saved consumption power, incorporating a plurality of sound sources or reflecting plates, and a reaction container is located between one of the sound sources and another of the sound sources or one of the reflecting plates, whereby sound waves can be irradiated toward the reaction container in several directions in order to efficiently fluidize a solution in the reaction container.

5 Claims, 10 Drawing Sheets

CHEMICAL ANALYSIS APPARATUS AND CHEMICAL ANALYSIS METHOD

BACKGROUND OF THE INVENTION

The present invention relates to a chemical analysis apparatus, and in particular to a chemical analysis apparatus incorporating an agitating mechanism for mixing a reagent and a sample with each other within a reaction container.

JP-A-8-146007 discloses a method of agitating a sample and a reagent in a noncontact manner by irradiating ultrasonic waves toward an opening of a reaction container containing therein the sample and the reagent, from a position below the container in order to mix the sample and the reagent with each other in a noncontact manner with no use of a spatula or a screw.

Further, JP-A-2000-146986 discloses such a technology that sound waves are irradiated to a reaction container containing therein a substance to be agitated (a sample and a reagent), laterally of the container, in order to agitate the substance in the container, in addition to irradiation of sound waves to the container toward the opening of the container from a position below the container.

Further, JP-A-2001-242177 discloses such a configuration that the means for irradiating sound waves to the container from a position below the container, which is disclosed in the JP-A-2000-146986 is a reflecting plate.

However, in such a case that a substance using a bit of a sample is efficiently agitated in a container so as to carry out an analysis, it has been found that the well-known above-mentioned configurations are insufficient. For example, with a configuration in which sound waves are irradiated from a position below the container toward the opening of the container, or sound wave are irradiated from one side of the container, should strong sound waves be irradiated from a sound wave supply means which is disclosed in the above-mentioned documents and which is located below the container in order to apply a strong agitating power, the liquid surface of the sample would swell upward so as to cause such a risk that a sample solution scatters. On the contrary, should weak sound waves be irradiated, no contribution to sufficient agitation would be obtained.

BRIEF SUMMARY OF THE INVENTION

The present invention is devised in order to solve the above-mentioned problems inherent to prior art, and accordingly, an object of the present invention is to provide a chemical analysis apparatus incorporating a mechanism for efficiently agitating a substance to be agitated.

To the end, according to a general concept of the present invention, there is provided such a mechanism that sound waves are irradiated to a substance to be agitated in a container in several directions in which a wall of the container is laid behind the substance to be agitated.

Specifically, according to a first aspect of the present invention, there is provided a chemical analysis apparatus incorporating a placing portion in which a reaction container containing therein a substance to be analyzed is placed, a sound wave supply portion spaced from the substance to be analyzed, for irradiating sound waves to the substance to be analyzed, and a measuring portion for measuring physical properties of the substance to be analyzed, characterized in that a first sound wave fed from the sound supply portion is irradiated to a position corresponding to a first part of the reaction container, a second sound wave is irradiated to a position corresponding to a second part of the reaction container, and the first and second sound waves are irradiated from a position where a wall of the reaction container is located behind the substance to be analyzed, as viewed in a direction in which the sound waves are propagated.

In a first specific form of the first aspect of the present invention, the chemical analysis apparatus is characterized in that the first part is the one in which an interface of a fluid including the substance to be analyzed, contained in the reaction container, is defined, and the second part is the one which is located, being off from the first part to the bottom side of the reaction container. For example, in the case of liquid, it is not a part where the liquid is made into contact with the container, but a part where the liquid defines a liquid surface.

In a second specific form of the first aspect of the present invention, the second sound wave is the one which is reflected by a reflecting means. This reflecting means is adapted to irradiate a sound wave reflected below the sound waves fed from the sound wave supply portion.

In a third specific form of the first aspect of the present invention, the first sound wave is fed from a first sound wave supply portion, and the second sound wave is fed from a second sound wave supply portion.

In a fourth specific form of the first aspect of the present invention, the reflecting means comprises a reflecting plate having a sound wave reflecting surface which is concave. Alternatively, the reflecting means is adapted to reflect reflected sound waves which are converged toward a zone where the reaction container is placed.

In a fifth specific form of the first aspect of the present invention, the sound wave supply portion is formed of a single piezoelectric vibrator having an outer surface formed thereon with an electrode which is split.

In a sixth specific form of the first aspect of the present invention, there is further incorporated a mechanism for changing the energy of the sound waves irradiated to the substance to be analyzed.

According to a second aspect of the present invention, the first sound wave irradiated to a position at which the reaction container is placed, is fed from a location that is spaced from a location where the second wave irradiated to the position at which the reaction container is placed, is fed, the reaction container intervening between two locations.

According to a third aspect of the present invention, the first sound wave irradiated to a position at which the reaction container is place, is fed from a location that is spaced from a location where the second wave irradiated to the position at which the reaction container is placed, is fed, the reaction container intervening between two locations. Further, the reaction container is placed between the first sound wave supply portion and the second sound wave supply portion.

As mentioned above, in the present invention, there is provided a means for mixing a sample and a reagent in a noncontact manner, in the chemical analysis apparatus incorporating, for example, a reaction container having an opening, sample, reagent and diluent supply means for supplying the sample, the reagent and diluent into the reaction container through the opening thereof so as to obtain a solution to be measured in the reaction container, and a means for measuring physical properties of the solution to be measured during reaction or after completion of the reaction. This mixing means is provided outside of the reaction container, and is provided with a sound wave producing means for irradiating sound waves in parallel with a liquid surface of the solution to be mixed in the reaction container, or obliquely to the liquid surface in a direction from a liquid phase to a gas phase, a means for reflecting sound waves passing through the solution to be measured, so as to introduce the reflected sound wave again into the reaction container, and a mechanism for producing the sound waves while changing their energy. With this arrangement, the mixing of the sample and the reagent can be effective in a non-contact manner.

Other objects, features and advantages of the invention will become apparent from the following description of the embodiments of the invention taken in conjunction with the accompanying drawings.

DETAILED DESCRIPTION OF THE INVENTION

Explanation will be hereinbelow made of embodiments of the present invention with reference to the accompanying drawing. It is noted that the present invention should not be limited only to configurations of the embodiments which will be explained, but the present invention can have any other various configurations.

A chemical analysis apparatus in these embodiments may be composed of an automatic sample pipetting mechanism for feeding a sample to be analyzed into a reaction container, an automatic reagent pipetting mechanism for feeding a reagent into the reaction container, an automatic agitating mechanism for agitating the sample and the reagent in the reaction container, a measuring unit for measuring physical properties of the sample during reaction or after completion of the reaction, an automatic washing mechanism for sucking and discharging the sample after the measurement, and for washing the reaction container, and a control mechanism for controlling the operation of the above-mentioned components.

Figure 1:
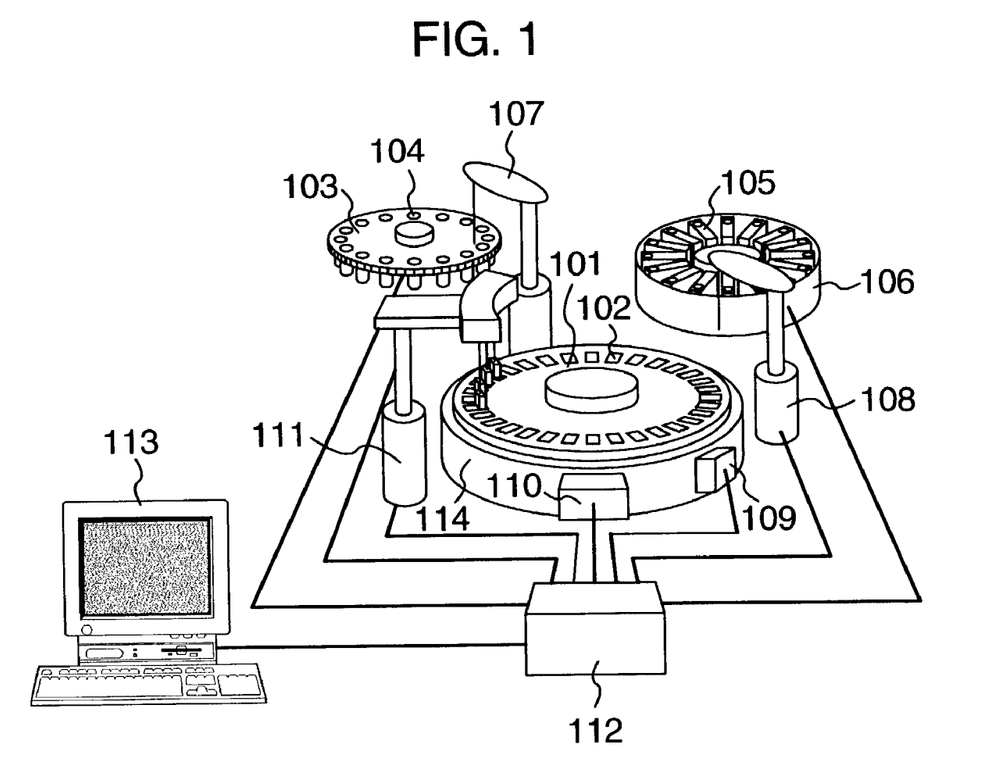
FIG. 1 is a perspective view illustrating an entire configuration of a chemical analysis apparatus in an embodiment of the present invention.

Explanation will be made of a first embodiment of the present invention with reference to FIGS. 1 and 2. FIG. 1 is a perspective view illustrating a configuration of a chemical analysis apparatus in the first embodiment of the present invention, and FIG. 2 is a vertically sectional view illustrating a configuration of an agitating mechanism of non-intrusion type (non-contact type) incorporated in the chemical analysis apparatus of the first embodiment shown in FIG. 1, for agitating and mixing a substance to be agitated, in a non-contact manner.

The chemical analysis apparatus in the first embodiment is mainly composed of a reaction disc 101 for accommodating reaction containers 102, a constant temperature tank 114 for holding a constant temperature condition of the reaction containers accommodated in the reaction disc, a sample turntable 103 for accommodating sample cups 104, a reagent turntable for accommodating reagent bottles 105, a sample pipetting mechanism 107 for pipetting a sample into a reaction container, and a reagent pipetting mechanism 108 for pipetting a reagent into the reaction container, an agitating mechanism 109 for agitating the pipetted sample and reagent in the reaction container 102, an optical measuring mechanism 110 for measuring a light absorbance of the mixed substance in the reaction container during a reaction process or after the reaction process, and a washing mechanism 111 for washing the reaction container after the measurement (of light). The above-mentioned components are operated under control by a program which is automatically prepared by the controller 112 in accordance with data (analysis items, a liquid quantity to be analyzed and the like) which is previously set up on a console 113 before the measurement is initiated.

Figure 2:
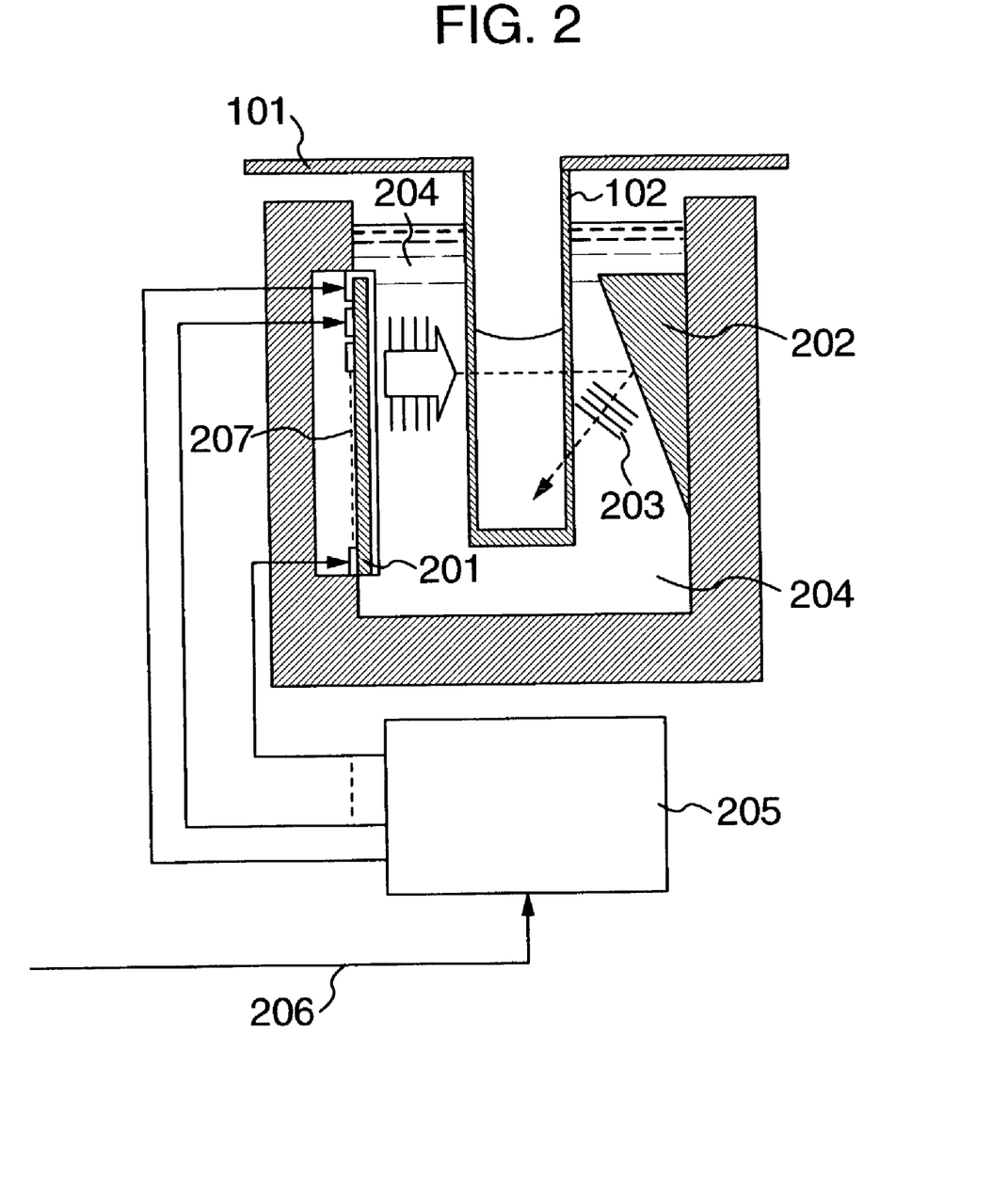
FIG. 2 is a vertically sectional view illustrating a part of the embodiment illustrated in FIG. 1, in detail.
Figure 5A:
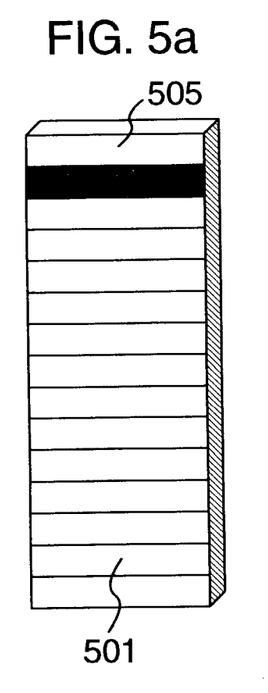
FIGS. 5a to 5b are views for explaining a sound source in the chemical analysis apparatus according to the present invention.
Figure 5B:
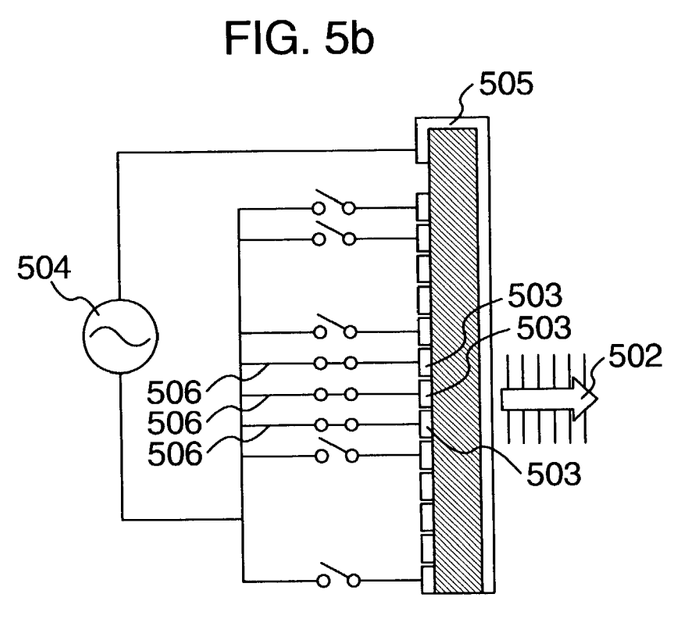
Figure 6A:
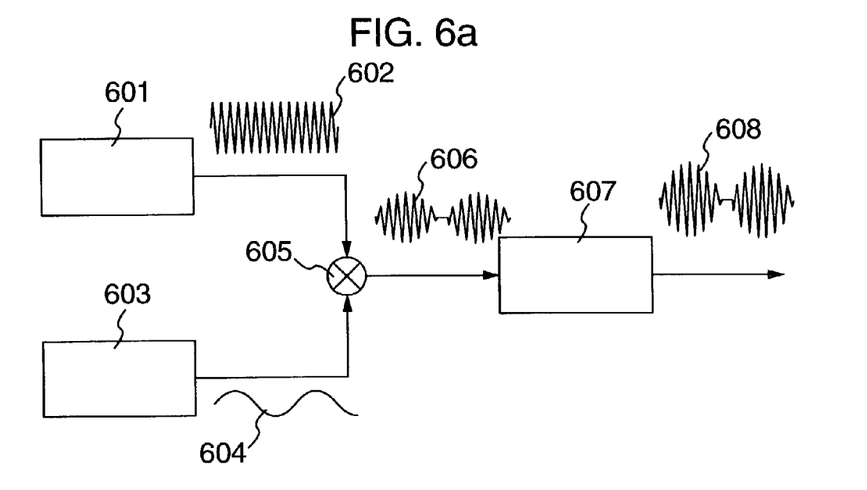
FIGS. 6a to 6b are views for explaining the operation of a drive system for the sound source in the chemical analysis apparatus according to the present invention.

The above-mentioned agitating mechanism 109 is composed of, as shown in FIG. 2, a sound wave producing means 201 (which will be referred to simply as "a sound source") provided, external to and lateral of the reaction container 102, and a sound wave reflecting means 202 (which will be referred to simply as "reflector") for reflecting sound waves propagated through the reaction container so as to introduce the sound wave again into the reaction container. The sound source has such a structure that segments 501, 503 are arranged in an array, as shown in FIGS. 5a and 5b so that they can be driven, independent from each other, and accordingly, those of the segments which are appropriate are selected by drivers 504, 506 through the intermediary of switches or the like in order to irradiate sound waves from an optional position 502. Further, the driver is composed therein of, as shown in FIG. 6a which is a block diagram, a wave form producing device 601 for producing an oscillation waveform 602 having a fundamental frequency of sound waves to be irradiated, and an auxiliary waveform producing device 603 for producing an oscillation wave form 604 having a frequency lower than that of the oscillation waveform 602, a multiplying circuit 605 for creating a multiplied waveform 606 between the both waveforms 602, 604, and a power amplifier 607 for power-amplifying the multiplied waveform 606. The above-mentioned driver is adapted to apply a voltage 608 which has been amplitude-modulated to piezoelectric elements.

Explanation will be hereinbelow made of the operation of the above-mentioned chemical analysis apparatus. A sample is pipetted from a sample cup 104 into a reaction container 102 by means of the sampling mechanism 107. Next, the turntable accommodated therein with the reaction container 102 is turned so that the reaction container 102 comes to a reagent pipetting position where a reagent is pipetted into the reaction container from a reagent bottle 106 by means of the reagent pipetting mechanism 108. Further, the turntable is turned so that the reaction container 102 comes to a position where the agitating mechanism 105 is provided, and where the sample and the reagent in the reaction container are agitated. After completion of the agitation, measurements are started, and after completion of the reaction the mixture of the sample and the reagent is sucked up by the washing mechanism 111 for washing the reaction container. The above-mentioned process steps in series are successively carried out for each of a plurality of samples in a batch.

Next, explanation will be made of the operation of the apparatus for agitating a substance to be agitated in the reaction container in a noncontact manner with reference to FIG. 2 which is a vertically sectional view illustrating the agitating device. There is provided a sound wave producing portion (which is a sound wave reflecting means 202 in this embodiment) for irradiating sound waves to the lower part of the reaction container in order to agitate a solution including a sample in the reaction container. Specifically, for example, there may be provided such a configuration that the reaction container 102 is located between the sound wave producing means 201 and the sound wave reflecting means 202. In this embodiment shown in FIG. 2, sound waves produced from the sound wave producing means 201 are reflected by the sound wave reflecting means 202 located on the opposite side, and are then fed into the reaction container. Next, explanation will be made of the basic operation thereof. A driver circuit 205 incorporating a driver and switches for the sound source, connected to the main controller 112 for the entire apparatus, receives data 206 relating to a quantity of a solution to be agitated, that is, a quantity of the sample and the reagent which have been pipetted in the reaction container, and a timing for agitating thereof. At first, the driver circuit 205 calculates a height 208 of the liquid surface of a solution to be measured, which is charged in the reaction container, from data relating to the liquid quantity in order to determine an optimum sound wave irradiating zone including the liquid surface, and selects segments 207 in the sound source, corresponding to the irradiating zone in order to drive the sound source. Since the driver circuit causes a piezoelectric element in the sound source to deliver a voltage having a waveform which has been amplitude-modulated, the sound wave to be irradiated are produced in accordance with variations in the amplitude thereof. The irradiated sound waves are propagated to the reaction container through the constant temperature bath 204, and are introduced into the reaction container. In general, if sound waves which have been propagated through liquid comes to a free liquid surface, a force with which liquid scatters into a gas phase is exerted (which is mainly caused by acoustic radiation pressure) to the liquid. At this stage, in this embodiment, since the voltage having a waveform which has been amplitude-modulated is delivered the sound source from the driver circuit, the sound waves to be irradiated are also dependent upon variation in the amplitude thereof. It is noted that the sound waves which are introduced into the reaction container after reflection, are propagated in a direction toward a position where no liquid surface is present.

Further, the sound reflecting means 202 is provided behind the reaction container in the direction of propagation of the sound waves, with respect to the sound wave producing means 201, and accordingly, it is possible to restrain the sound waves produced by the sound wave producing means 201 from causing damage to peripheral equipment, or the like.

Figure 3A:
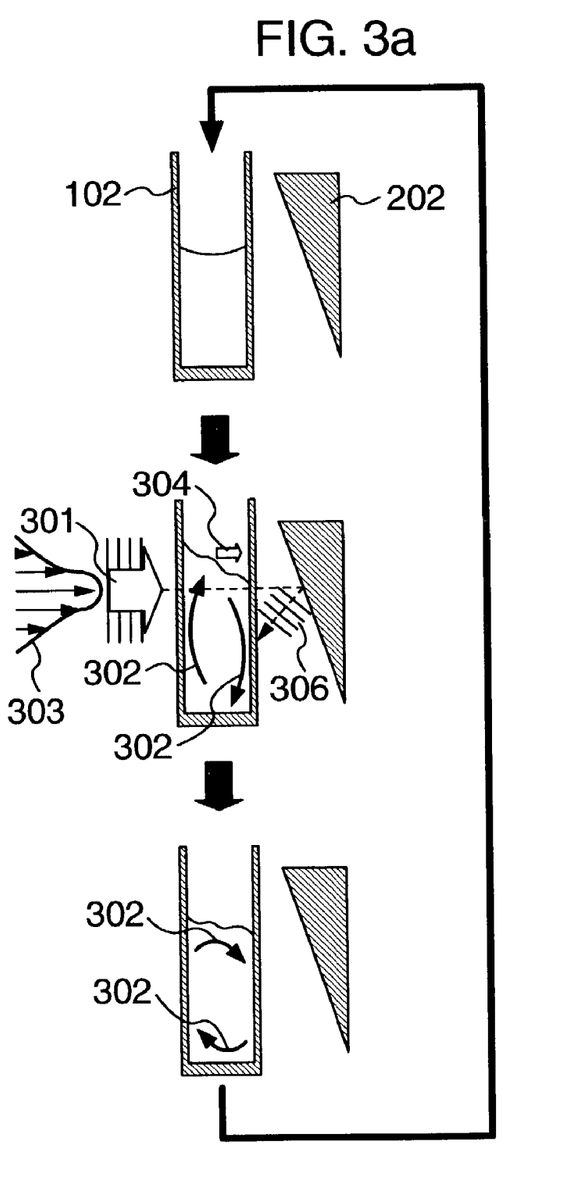
FIGS. 3a to 3b are views for explaining a fluidization principle during agitation in the chemical analysis apparatus according to the present invention.
Figure 3B:
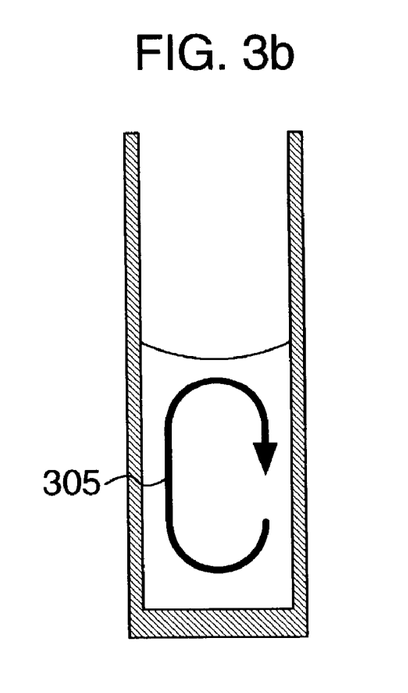

If an intermittent sound wave 201 is irradiated as shown in FIG. 3a, the force is exerted to the liquid surface so as to crease a kind of a wave on the liquid surface in the reaction container. Further, the sound wave 301 is irradiated in a beam-like shape having an intensity distribution 303 as shown in the figure, and accordingly, a part thereof is transmitted through the reaction container as indicated by the dotted line. The transmitted sound wave is reflected by the reflector 202, and is again introduced (203) into the reaction container. By the way, since a sound flow or an acoustic radiation pressure is produced when sound waves are propagated through liquid, the reintroduction of the transmitted sound wave causes such an effect that the liquid is fluidized in the sound propagating direction. At this time, the direction of the propagation of the sound wave which is reintroduced into the reaction container is set so as to be not directed toward the opening of the container (that is, for example, toward a position where no liquid surface is present), and accordingly, it is possible to restrain the liquid from scattering outside of the reaction container even though the intensity of the sound wave is increased. Due to the fluidization of the liquid accompanied with the wave produced at the liquid surface, and the fluidization caused by the reintroduction of the sound wave through the reflection, the liquid is fluidized as indicated by the arrow 302. With the repetitions of irradiation of the above-mentioned intermittent sound wave, a swirl flow 305 is produced in the liquid in the reaction container as shown in FIG. 3b. In the chemical analysis apparatus according to the present invention, there is used a means for mixing a sample and a reagent with the use of the swirl fluidization in a non-contact manner with respect to the liquid.

With the configuration of this embodiment, it is possible to prevent the liquid from scattering in comparison with such a case that sound waves are irradiated from a position external to and below the reaction container toward the opening of the latter. Further, the agitation in this embodiment is effective by applying a suitable sound intensity distribution to the liquid to be measured within the reaction container. Further, in this embodiment with the use of the fluidization whose acoustic radiation pressure is dominant in the vicinity of a liquid interface which is not affected by a friction of the wall surface of the reaction container, the liquid to be measured can be agitated and mixed by sound waves having a smaller intensity in comparison with such a method which utilizes only acoustic fluidization. Further, since sound waves having propagated through the reaction container is again reintroduced into the latter so as to promote the fluidization in the bottom part of the reaction container, the produced sound waves can be effectively used.

Further, since the mixing can be made with a completely noncontact manner with respect to the liquid to be measured contained in the reaction container, agitation with carry-over-less and a bit of liquid can be carried out in a chemical analysis apparatus. Thereby it is possible to materialize a function capable of performing high speed analysis.

Further, it is possible to provide a configuration which is preferable for several inspection items which can accept reagents and samples which have liquid quantities and liquid physical properties in a wide range.

Further, it is possible to carry out the agitation with carry-over-less and a bit of liquid, and to reduce the consumption power.

Further, it is possible to avoid problems including carry-over and contamination caused by sticking inherent to an agitating process with the use of a spatula or a screw, and positioning accuracy caused by miniaturization of the reaction container.

It is specifically noted that since a sample can be agitated effectively, if the present invention is applied in a chemical analysis apparatus capable of performing a high speed process with a high degree of accuracy, in which several samples can be analyzed in a batch with a short time, the time by which a result of an inspection can be obtained after the inspection is completed can be shortened.

Further, even though a sample extracted from a patient or the like is reduced, the sample can be effectively agitated. Thereby it is possible to reduce the quantity of waste liquid to be disposed after the inspection, and further, it is possible to reduce the running costs for the inspection.

It is noted that a sample and a reagent are automatically pipetted into each of reaction containers circumferentially accommodated in the turn table by a pipetter incorporating a robot arm, and a solution to be measured (the sample and the agent which have been pipetted into the reaction container) is mixed by means of the agitating mechanism. Further, a chemical reaction of the solution is measured, and the result of the inspection thereof is outputted. After completion of the measurement, the solution to be measured is sucked, and then, the reaction container is washed. Thus, the inspection of the sample is completed for one of several items thereof. Practically, in general, with the use of a chemical analysis apparatus capable of performing such a process that a plurality of inspections are carried out in sequence under control programmed by the user, of several manipulation steps (pipetting and agitating of the sample and the reagent, and washing of the reaction container), the step of agitating the solution to be measured can be effectively made, that is, it is possible to suppress deficiencies such as that no desired reaction can be fulfilled due to insufficient mixing caused by short-time agitation, and accordingly, precise inspection results cannot be obtained. Further, in the case of using a spatula for agitation, should a bit of a solution which has been used during inspection be carried by the spatula into a reaction container for a next inspection (carry-over), the problem of contamination would be caused. Thus, it is possible to prevent the solution to be measured from being decreased due to sticking to the spatula.

In the configuration disclosed in the above-mentioned JP-A-8-146007, in such a case that sound waves are irradiated to a reaction container from a position external thereto so as to apply a suitable sound intensity distribution in a substance to be agitated in the reaction container in order to induce acoustic fluidization, the smaller the quantity of a solution to be measured, the smaller the reaction container itself, resulting in reduction of the surface area of the reaction container, acoustic energy required for generating the acoustic fluidization can hardly be applied to the substance in the reaction container. Further, in order to create a circulation flow which is effective for the agitation, it is required to create a sharp intensity distribution of the sound field in the reaction container. However, in the case of a small-sized reaction container, relative intensity difference in the sound field is decreased, and accordingly, it is difficult to efficiently agitate the solution to be measured in a short time.

Next, detailed explanation will be made of the distinct features of the sound source and the drive system (around the drive circuit) which are used in this embodiment. Referring to FIG. 5a which shows the arrayed sound source as mentioned above, this embodiment utilizes such a convenient way that one of electrodes on both sides of a single piezoelectric element is divided into several parts 501. These divided electrode parts are selectively applied with a voltage 504, corresponding to a desired irradiating zone as shown in FIG. 5b, and accordingly, there can be materialized a sound source which is functionally equivalent to sound sources which are arranged in an array. It is noted that a part of the electrode on the side where the electrode is not divided is folded back onto the surface of the piezoelectric element on the side where the electrode is divided, as indicated by 505, the connection of electric wires from drivers can be concentrated to only one surface thereof. With the use of the single piezoelectric element applied with the electrodes which are fabricated as mentioned above, the costs of the agitating mechanism can be reduced. The configuration of this sound source is advantageous in view of the mass production base thereof, and with the use of an electrode pattern produced by screen printing or the like, the time required for manufacturing the agitating mechanism can be shortened. Further, since the structure thereof is relatively simple, the agitating mechanism is highly reliable. Further, in comparison with a conventional spatula incorporating a robot arm, the size of the agitating mechanism can be greatly reduced, thereby it is possible to contribute to miniaturization of the entire apparatus.

In this embodiment, with the provision of such a feature that pulsation can be applied to a swirl flow in the reaction container by changing, in time, the intensity of ultrasonic waves to be irradiated in the agitating mechanism, the mixing can be enhanced thereby so as to shorten the time required for the agitation, and to save consumption power.

Figure 6B:
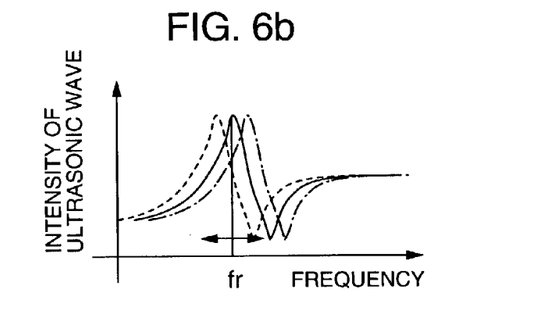
Figure 6C:
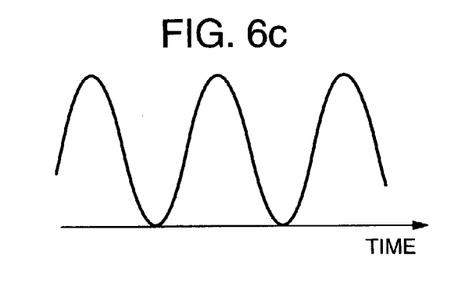
Figure 6D:
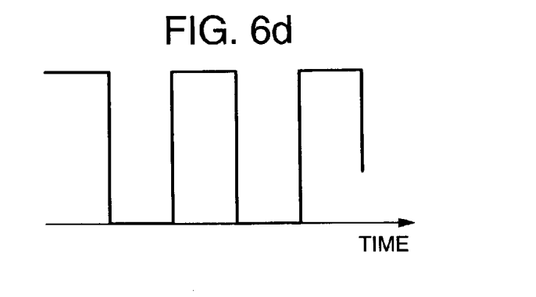

As to a wave form which is used as a subwaveform for amplitude modulation, there may be used a rectangular waveform which repeats turn-on and -off as shown in FIG. 6b, in addition to a waveform as shown in FIG. 6a, in which it sinusoidally varies between its minimum value and its maximum value. In this case, a relatively simplified waveform creating mechanism can be used, thereby it is possible to reduce the costs of the driver. Further, the above-mentioned turn-on and -off operation can be made only by turning on and off the driver which produces only a fundamental frequency of sound waves, thereby it is possible to further reduce the costs of the driver.

Figure 4A:
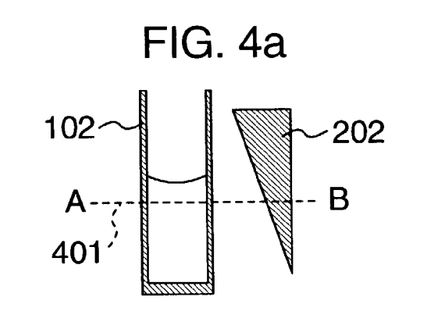
FIGS. 4a to 4c are sectional views illustrating various possible configurations of a reflector shown in FIG. 2.
Figure 4B:
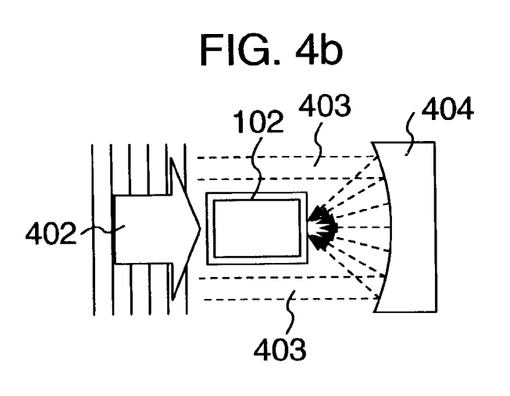
Figure 4C:
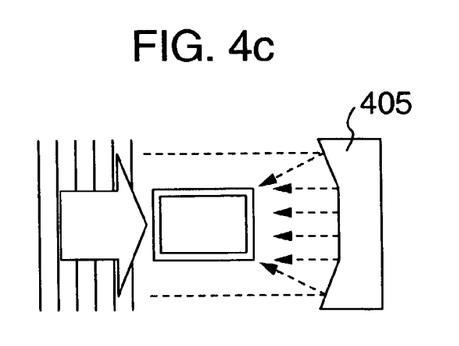

Further, as to another measures for saving consumption power, there may be used such a method that the reflecting surface of the reflector 202 is fabricated. FIGS. 4b and 4c are sectional views along line A-B shown in FIG. 4a, illustrating the reaction container 102 and the reflector 202 which have been explained hereinabove. Specifically, FIG. 4b shows a pattern of sound rays in which sound waves 401 irradiated from the left side of the figure is propagated through the reaction container, and is reflected by the reflector so as to be again introduced into the reaction container. As shown in Figure, since the reflecting surface is fabricated in a spherical shape, reflected sound waves can be converged to one single point due to an effect similar to that of a parabola antenna. Since the intensity of the sound waves is increased, correspondingly, at a position where the sound waves are converged, if the converged point is set to a suitable position (for example, the center of the reaction container), the fluidization with a high degree of efficiency can be obtained. FIG. 4c shows an example in which the sound waves 403 propagated outside of the reaction container are reflected toward the reaction container. In this case, the surface at which the propagated waves are reflected, is set to be perpendicular to the propagated waves, and a surface at which the sound waves 403 propagated outside of the reaction container is reflected is fanned so as to direct the reflected waves toward reaction container. In either of the cases, the sound waves 403 propagated outside of the reaction container can be effectively used, and can be also converged together with the sound waves propagated through the reaction container, thereby it is possible to enhance the intensity of the sound waves to be reintroduced into the reaction container.

In the case of using a piezoelectric element in a sound source, there may be used a thickness resonance of the piezoelectric element. In the case of manufacturing such a sound source on a mass production base, unevenness among piezoelectric elements would be possibly serious due to trade-off between manufacturing costs and machining accuracy. Referring to FIG. 6b which schematically shows frequency response characteristics of three piezoelectric elements (they are fabricated with their uneven thicknesses) around their thickness resonances, it will be found that uneven thicknesses of piezoelectric elements cause uneven resonant frequencies with which the piezoelectric elements produce output powers with maximum intensity. Accordingly, such a problem that unevenness among piezoelectric elements would be serious can be solved by frequency modulation to the frequency of sound waves around their resonant frequencies. In the above-mentioned embodiment, although the waveform producing device 601 for producing the oscillation frequency wave 602 having a single frequency has been explained, with the provision of a function capable of frequency-modulation around a resonant frequency with a suitable frequency width in this waveform producing device 601, individual differences among piezoelectric elements can be absorbed.

The essential feature of the present invention is the provision of such a configuration that in order to mix a sample and a reagent with each other, first, sound waves are irradiated in a direction toward the liquid surface of a solution so as to create a wave at the liquid surface, and second, sound waves are irradiated to the solution in another direction in order to enhance the efficiency of the fluidization of the solution, that is, to efficiently mix the sample and the reagent. In the above-mentioned embodiment, a part of the sound waves irradiated toward the liquid surface of the solution and propagated through the reaction container is reintroduced into the reaction container with the use of the reflector, and accordingly, two way irradiation can be materialized with the use of a single sound source.

Next, explanation will be hereinbelow made of another embodiment in which the irradiation is made in two ways.

Figure 7:
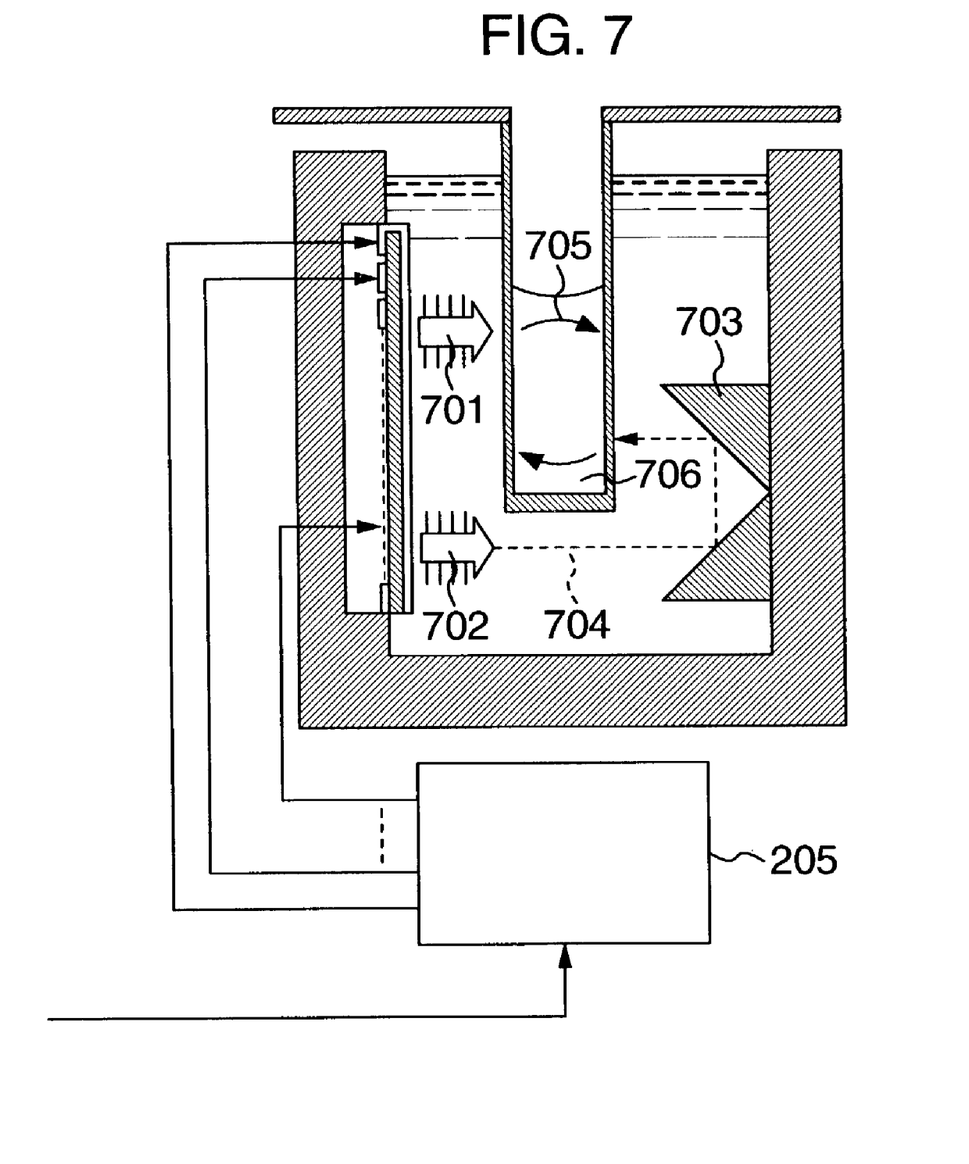
FIG. 7 is a schematic view illustrating another embodiment of the present invention.

Referring to FIG. 7 which shows a second embodiment of the present invention, this second embodiment has a configuration similar to the first embodiment, comprising a single sound source and a reflector, except that it has a different transmission path 704 through which sound waves are irradiated to the lower part 706 of the inside of the reaction container. The embodiment shown in FIG. 7 is the same as that of the embodiment shown in FIG. 2 in which the sound waves 701 are irradiated toward the liquid surface. However, sound waves 702 irradiated for fluidizing the solution in the bottom part of the reaction container are propagated outside of the reaction container, as indicated by the arrow 704, by means of the reflector 703, and is then introduced into the reaction container so as to create fluidization 705 of the solution in the bottom part of the reaction container. In this embodiment, as a result, although two kind of waves are produced from the sound source, with the use of the array-like sound source shown in FIG. 5, the above-mentioned production of the sound waves can be simply made. As stated above, even with the configuration shown in FIG. 7, a high degree of efficiency of mixing similar to that of the embodiment shown in FIG. 2 can be obtained.

Figure 8:
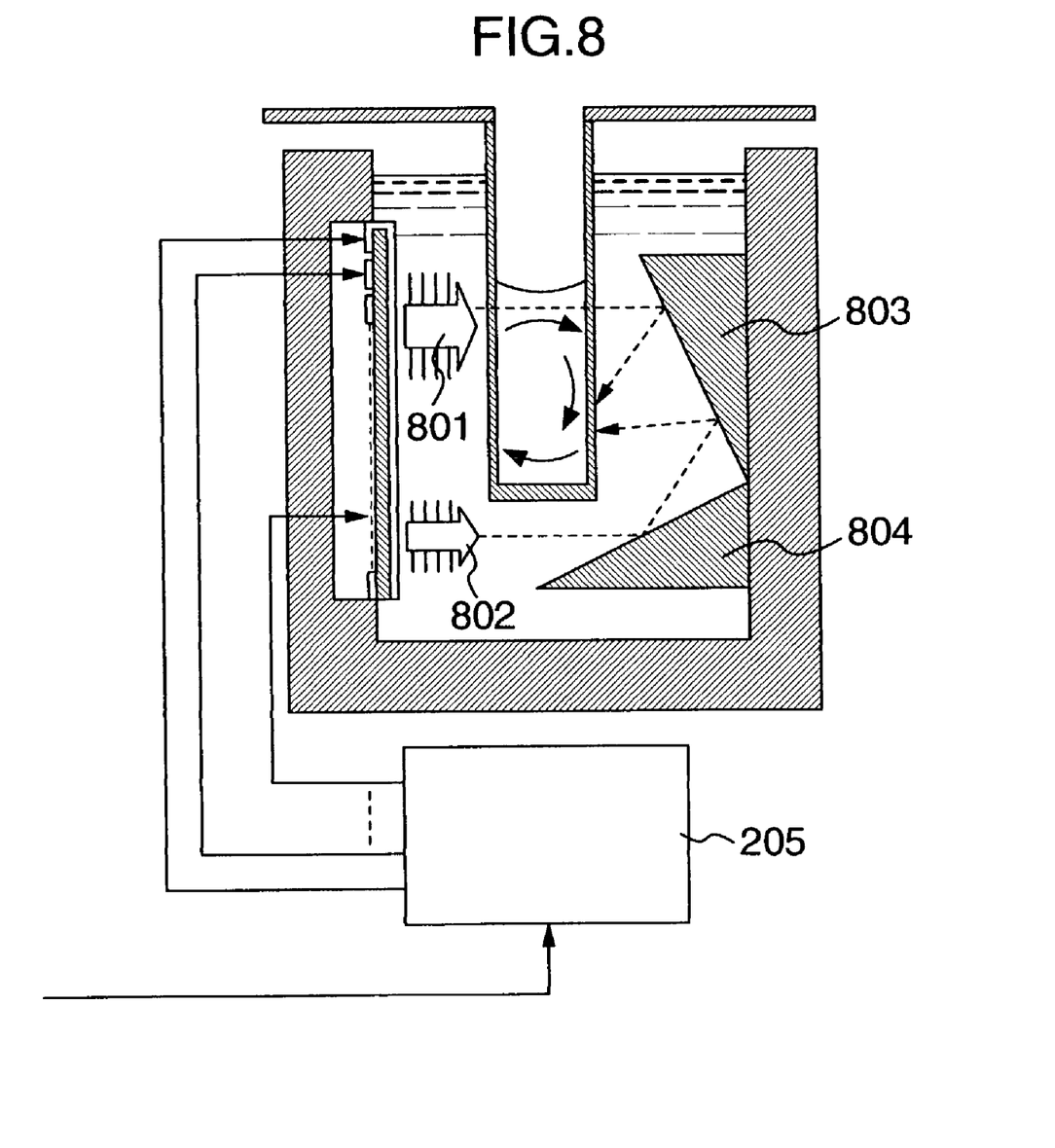
FIG. 8 is further another embodiment of the present invention.

Further, in another embodiment shown in FIG. 8, which can materialize both configurations shown in FIGS. 2 and 7. That is, it is composed of a reflector 803 which reflects sound waves 801 irradiated toward the liquid surface of a solution in a reaction container so as to reintroduce the sound waves into the bottom part of the reaction container, similar to the embodiments shown in FIGS. 2 and 7, and a reflector 804 which propagates sound wave outside of the reaction container and then introduces sound waves in the bottom part of the reaction container, similar to the embodiment shown in FIG. 7. With this configuration, it is possible to aim at synergistically fluidizing the solution in the bottom part of the reaction container.

Figure 9:
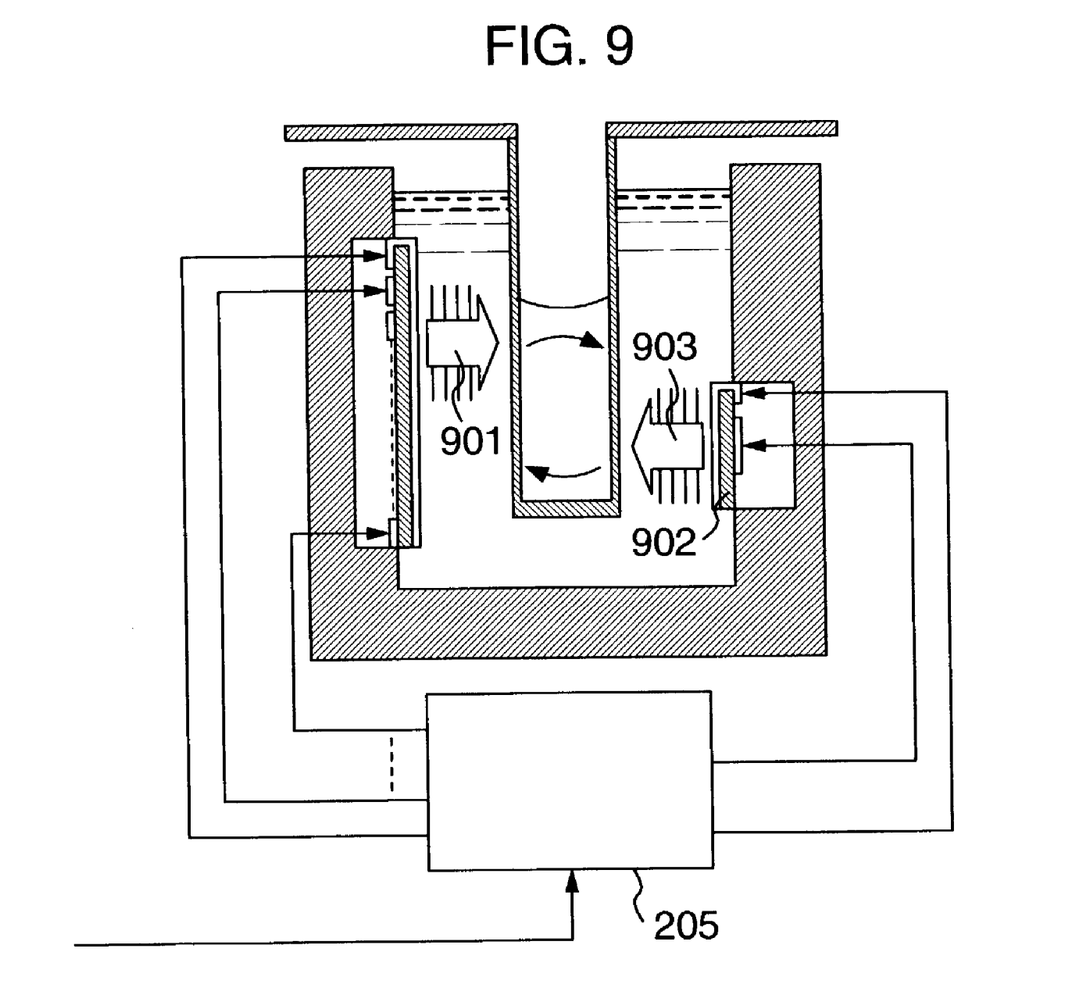
FIG. 9 is further another embodiment of the present invention.

Although the present invention has been explained in the form of the preferred embodiments as mentioned above, in which a single sound source and a reflector are used, as shown in FIGS. 5a and 5b, so as to irradiate sound waves in two directions toward the liquid surface of a solution in the reaction container and the bottom part of the reaction container, respectively, the same technical effects and advantages can be attained by such a configuration that two sound sources are arranged, independent from each other so as to sound waves are irradiated toward the liquid surface of the solution in the reaction container and the bottom of the reaction container, respectively. FIG. 9 shows an embodiment having this configuration. In this embodiment shown in FIG. 9, sound waves 901 irradiated toward the liquid surface of a solution in the reaction container are similar to that explained in the aforementioned embodiments, but another sound source 902 is provided, instead of the reflector which is used in the aforementioned embodiments, so as to irradiate sound waves 903 toward the bottom part of the reaction container.

It is noted that the reflector is an important component, in addition to the sound source, in any of the embodiments shown in FIGS. 2, 7, 8 and 10. In general, the greater the difference in acoustic impedance (which is the product of a density of a medium and a sound velocity) between two media at the interface therebetween, the higher the reflectivity. Thus, in the embodiments of the present invention, the reflectors for reflecting sound waves propagated through the water 204 (in the constant temperature bath 204) are made of SUS. However, it may be made of any of materials which satisfy the above-mentioned condition, that is, a great difference in the acoustic impedance between water and the material, instead of SUS.

Figure 10:
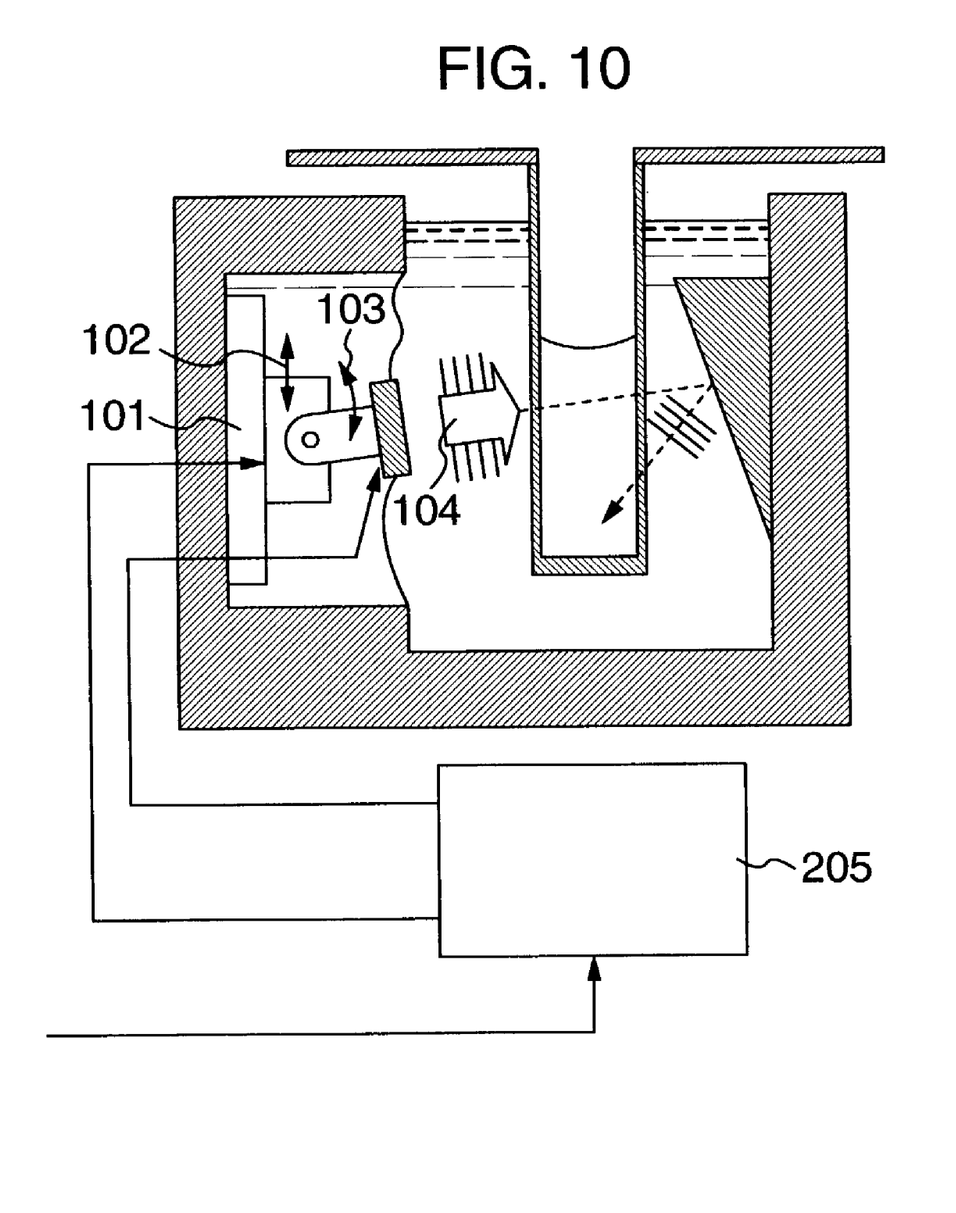
FIG. 10 is further another embodiment of the present invention.

In the embodiments stated hereinabove, the sound source composed of a piezoelectric element with divided electrode pieces arranged in an array is used, as shown in FIGS. 5a and 5b, in order to control the sound wave irradiating position which depends upon a liquid quantity, that is, a liquid surface height which is different among inspection items. However, it goes without saying that a sound source incorporating a shift mechanism, as shown in FIG. 10, may be used, instead of the above-mentioned sound source. In the embodiment shown in FIG. 10, the vertical shift 102 and the fanning 103 thereof can be controlled, and accordingly, the direction of sound waves to be irradiated toward the liquid surface of a solution in the reaction container can be optionally adjusted. Since the direction of the sound waves irradiated toward the liquid surface can be adjusted, thereby it is possible to optimumly control the waveform created at the liquid surface.

Further, in the embodiments which have been hereinabove explained, the sound waves are irradiated in two or three directions. It may be irradiated in much more directions.

Although there have been explained in the above-mentioned embodiments the configuration of the agitation for mixing a sample and a reagent in a noncontact manner, this configuration may also be effective for fluidization of washing liquid in a reaction container which is washed by the washing mechanism 111 shown in FIG. 1.

The present invention can be materialized as an analysis device such as a biochemical analysis apparatus, an immune analysis apparatus, a DNA analysis apparatus or the like, a medicine preparing apparatus or an agitating apparatus.

According to the present invention, it is possible to provide a chemical analysis apparatus which can be efficiently agitate a substance to be agitated.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A chemical analysis apparatus comprising a reaction container containing therein a substance to be analyzed, said reaction container being located in fluid of an analysis tank, an agitating mechanism spaced from the substance to be analyzed, for mixing a mixture of the substance to be analyzed and liquid together in the reaction container and agitating them, and a measuring portion for measuring physical properties of the substance to be analyzed, wherein said agitating mechanism has both a sound supply portion adapted to irradiate sound waves unilaterally in one direction through the mixture to apply a lateral sound-wave force to the mixture, and a reflector disposed on an internal wall of said analysis tank, on a substantially opposite side to said sound supply portion with respect to the reaction container, the reflector including an upper and a lower flat reflector surfaces which intersect each other and which are each slanted relative to the internal wall of the analysis tank, where each of the upper and lower flat reflector surfaces reflects the sound waves irradiated through the mixture, to the other of the upper and lower flat reflector surfaces, and the other of the upper and lower flat reflector surfaces reflects the sound waves back toward the mixture at a vertical location which is separated from a vertical location where the sound wave is irradiated, so as to introduce said reflected sound waves again into the mixture to apply a reflected lateral sound wave force to the mixture in a direction opposite to the one direction, where the sound waves and reflected sound waves are applied without counteracting sound waves and counteracting reflected sound waves from opposing sides of the reaction container, and where a combined force of the lateral sound-wave force applied by the sound supply portion and the reflected sound-wave force applied by the reflector, induce a swirling circulation flow of the mixture of said liquid and said substance around an inside of said reaction container.

2. A chemical analysis apparatus as set forth in claim 1, wherein said sound supply portion has a plurality of segments for a sound source.

3. A chemical analysis apparatus as set forth in claim 1, wherein said sound supply portion is composed of a single piezoelectric element having a surface formed thereon with an electrode which is divided.

4. A chemical analysis apparatus as set forth in claim 1, wherein said sound supply portion comprises a changer unit adapted to change energy of the sound waves to be produced.

5. A chemical analysis apparatus comprising a supply portion for supplying a substance to be analyzed and a reagent or a diluent together as a mixture, a reaction container having an opening and containing therein the mixture of the substance to be analyzed and the reagent or the diluent, said reaction container being located in a fluid of an analysis tank, a sound supply portion spaced from the substance to be analyzed and adapted to irradiate sound waves unilaterally in one direction through the mixture to apply a lateral sound-wave force to the mixture, and a reflector disposed on an internal wall of said analysis tank, on a substantially opposite side to said sound supply portion with respect to the reaction container, the reflector including an upper and a lower flat reflector surfaces which intersect each other and which are each slanted relative to the internal wall of the analysis tank, where each of the upper and lower flat reflector surfaces reflects the sound waves irradiated through the mixture, to the other of the upper and lower flat reflector surfaces, and the other of the upper and lower flat reflector surfaces reflects the sound waves back toward the mixture at a vertical location which is separated from a vertical location where the sound wave is irradiated, so as to introduce said reflected sound waves again into the mixture to apply a reflected lateral sound wave force to the mixture in a direction opposite to the one direction, where the sound waves and reflected sound waves are applied without counteracting sound waves and counteracting reflected sound waves from opposing sides of the reaction container, and where a combined force of the lateral sound-wave force applied by the sound supply portion and the reflected sound-wave force applied by the reflector, induce a swirling circulation flow of the mixture of said liquid and said substance around an inside of said reaction container.

* * * * *